United States Patent
Mitrea et al.

(10) Patent No.: US 12,131,818 B2
(45) Date of Patent: Oct. 29, 2024

(54) SYSTEMS AND METHODS FOR PROVIDING SURGICAL GUIDANCE

(71) Applicant: Activ Surgical, Inc., Boston, MA (US)

(72) Inventors: Bogdan Mitrea, Canton, MA (US);
Chibueze Nwaiwu, Boston, MA (US);
Alyson Dechert, Boston, MA (US);
Peter Kim, Boston, MA (US); Tina P. Chen, Cambridge, MA (US)

(73) Assignee: ACTIV Surgical, Inc., Boston, MA (US)

( * ) Notice: Subject to any disclaimer, the term of this patent is extended or adjusted under 35 U.S.C. 154(b) by 0 days.

(21) Appl. No.: 18/323,623

(22) Filed: May 25, 2023

(65) Prior Publication Data
US 2024/0136045 A1 Apr. 25, 2024
US 2024/0233906 A9 Jul. 11, 2024

Related U.S. Application Data

(63) Continuation of application No. PCT/US2021/061854, filed on Dec. 3, 2021.
(Continued)

(51) Int. Cl.
*A61B 34/10* (2016.01)
*A61B 34/20* (2016.01)
(Continued)

(52) U.S. Cl.
CPC ............ *G16H 20/40* (2018.01); *A61B 34/10* (2016.02); *A61B 34/20* (2016.02); *G16H 30/40* (2018.01);
(Continued)

(58) Field of Classification Search
CPC ........ G16H 20/40; G16H 30/40; A61B 34/20; A61B 34/30; A61B 2034/2065
See application file for complete search history.

(56) References Cited

U.S. PATENT DOCUMENTS

| 8,406,859 B2 | 3/2013 | Zuzak et al. |
| 8,792,098 B2 | 7/2014 | Dewald et al. |

(Continued)

FOREIGN PATENT DOCUMENTS

| WO | WO-2006073915 A2 * | 7/2006 | ......... A61B 5/04001 |
| WO | WO-2010096447 A2 | 8/2010 | |

(Continued)

OTHER PUBLICATIONS

Dunn, et al. Laser speckle contrast imaging in biomedical optics. Journal of Biomedical Optics 15(1), 011109 (Jan./Feb. 2010).
(Continued)

*Primary Examiner* — Zade Coley
(74) *Attorney, Agent, or Firm* — Cesari and McKenna, LLP (57) ABSTRACT

The present disclosure provides systems and methods for providing surgical guidance. In one aspect, the present disclosure provides a surgical guidance system comprising: an image processing module configured to (i) receive image data obtained using one or more image and/or video acquisition modules and (ii) generate one or more medical predictions or assessments based on (a) the image/video data or physiological data associated with the image/video data and (b) one or more training data sets comprising surgical or medical data associated with a patient or a surgical procedure. The one or more training data sets may comprise anatomical and physiological data obtained using a plurality of imaging modalities. The system may further comprise a visualization module configured to provide a surgical operator with an enhanced view of a surgical scene, based on the one or more augmented data sets.

21 Claims, 4 Drawing Sheets

Related U.S. Application Data (60) Provisional application No. 63/121,802, filed on Dec. 4, 2020.

(51) Int. Cl.
 *G16H 20/40* (2018.01)
 *G16H 30/40* (2018.01)
 *A61B 90/00* (2016.01)

(52) U.S. Cl.
 CPC . *A61B 2034/107* (2016.02); *A61B 2034/2065* (2016.02); *A61B 2090/365* (2016.02)

(56) References Cited

U.S. PATENT DOCUMENTS

| | | |
|---|---|---|
| 8,823,790 B2 | 9/2014 | Dunn et al. |
| 8,891,087 B2 | 11/2014 | Zuzak et al. |
| 9,072,445 B2 | 7/2015 | Berguer et al. |
| 9,198,578 B2 | 12/2015 | Zuzak et al. |
| 9,220,570 B2 | 12/2015 | Kim et al. |
| 9,226,673 B2 | 1/2016 | Ferguson, Jr. et al. |
| 9,271,658 B2 | 3/2016 | Ferguson, Jr. et al. |
| 9,622,662 B2 | 4/2017 | Zuzak et al. |
| 9,788,903 B2 | 10/2017 | Kim et al. |
| 10,058,256 B2 | 8/2018 | Chen et al. |
| 10,089,737 B2 | 10/2018 | Krieger et al. |
| 10,244,991 B2 | 4/2019 | Shademan et al. |
| 10,390,718 B2 | 8/2019 | Chen et al. |
| 10,398,519 B2 | 9/2019 | Kim et al. |
| 10,675,040 B2 | 6/2020 | Kim et al. |
| 10,722,173 B2 | 7/2020 | Chen et al. |
| 10,792,492 B2 | 10/2020 | Chen et al. |
| 10,948,350 B2 | 3/2021 | Ferguson, Jr. et al. |
| 11,135,028 B2 | 10/2021 | Kim et al. |
| 11,278,220 B2 | 3/2022 | Tucker et al. |
| 2003/0139667 A1 | 7/2003 | Hewko et al. |
| 2008/0262344 A1 | 10/2008 | Brummett |
| 2012/0095354 A1 | 4/2012 | Dunn et al. |
| 2013/0245456 A1 | 9/2013 | Ferguson, Jr. et al. |
| 2013/0274596 A1 | 10/2013 | Azizian et al. |
| 2014/0171791 A1* | 6/2014 | Simon ............... A61B 5/0084 600/424 |
| 2016/0058517 A1 | 3/2016 | Kim et al. |
| 2017/0084012 A1 | 3/2017 | Walle-Jensen et al. |
| 2017/0249432 A1 | 8/2017 | Grantcharov |
| 2018/0250075 A1 | 9/2018 | Cho |
| 2018/0322254 A1 | 11/2018 | Smurro |
| 2018/0360543 A1 | 12/2018 | Roh et al. |
| 2019/0125361 A1* | 5/2019 | Shelton, IV ........... A61B 90/30 |
| 2019/0201145 A1 | 7/2019 | Shelton, IV et al. |
| 2020/0305721 A1 | 10/2020 | Chen et al. |
| 2020/0315432 A1 | 10/2020 | Tully et al. |
| 2021/0030277 A1 | 2/2021 | Ferguson, Jr. et al. |
| 2021/0282654 A1 | 9/2021 | Cha et al. |
| 2023/0352133 A1 | 11/2023 | Chen et al. |

FOREIGN PATENT DOCUMENTS

| | | |
|---|---|---|
| WO | WO-2010096453 A1 | 8/2010 |
| WO | WO-2012096878 A2 | 7/2012 |
| WO | WO-2014152753 A1 | 9/2014 |
| WO | WO-2016061052 A1 | 4/2016 |
| WO | WO-2016153741 A1 | 9/2016 |
| WO | WO-2017075602 A1 | 5/2017 |
| WO | WO-2019045971 A1 | 3/2019 |
| WO | WO-2020006454 A1 | 1/2020 |
| WO | WO-2021252384 A1 | 12/2021 |
| WO | WO-2022029308 A1 | 2/2022 |
| WO | WO-2022058499 A1 | 3/2022 |
| WO | WO-2022120199 A1 | 6/2022 |

OTHER PUBLICATIONS

Holstein-Rathlou et al. Nephron blood flow dynamics measured by laser speckle contrast imaging. Am J Physiol Renal Physiol 300: F319-F329, 2011.

PCT/US2021/036236 International Search Report and Written Opinion dated Nov. 4, 2021.

PCT/US2021/061854 International Search Report and Written Opinion dated Feb. 25, 2022.

Richards et al. Intraoperative laser speckle contrast imaging with retrospective motion correction for quantitative assessment of cerebral blood flow. Neurophotonics 1(1), 015006 (Jul.-Sep. 2014).

Richards et al. Low-cost laser speckle contrast imaging of blood flow using a webcam. 2013 Optical Society of America.

* cited by examiner

SYSTEMS AND METHODS FOR PROVIDING SURGICAL GUIDANCE

CROSS REFERENCE

This application is a continuation of International Patent Application PCT/US21/61854, filed Dec. 3, 2021, which claims priority to U.S. Provisional Application No. 63/121,802, filed Dec. 4, 2020, each of which is incorporated by reference herein in its entirety.

BACKGROUND

Surgeons may use anatomy and anatomic landmarks as a guide in making intraoperative surgical decisions during operations. Such anatomic landmarks make it easier for surgeons to gain and maintain visual orientation during surgical procedures, which can prevent unrecognized or unintentional injuries to altered or hidden critical structures due to individual variation or pathology. One strategy for minimizing injuries during a surgical procedure is the anticipatory identification of critical structures and the use of a critical view of safety, that is, an intraoperative view that portrays relevant anatomy necessary to minimize inadvertent tissue injury during a given procedure. Anatomic vision using light beyond the visible spectrum can also provide value, intraoperatively.

SUMMARY

Surgical guidance systems currently available may provide predictions of anatomic locations and contours of tissue structures based on standard intraoperative laparoscopic and robot assisted endoscopic datasets in the visual spectrum. Given the variations in patient anatomy, pathology, surgical techniques, and surgeon style, competence and proficiency, the precision and accuracy of such conventional systems are insufficient for clinical applications, and the feasibility of such systems is both hypothetical and impractical.

Recognized herein are various limitations with surgical guidance systems currently available. In view of the limitations associated with conventional surgical guidance systems based on human visual spectrum, the present disclosure provides artificial intelligence (AI)-based systems that can be utilized to improve a priori or anticipatory surgical outcomes.

The present disclosure generally relates to systems and methods for providing augmented visuals, real-time guidance, and decision support to surgeons and other operating assistants using artificial intelligence (AI). More specifically, the present disclosure provides systems and methods for intraoperative real-time prediction of the location of, and identification of critical structures and/or tissue viability before, during, and/or after surgical procedures using machine learning algorithms trained on any combination of white light-based images and/or videos, chemical signal enhancers such as fluorescent near-infrared (NIR) images and/or videos or radio-labelled dye imaging, indigenous chromophores, auto-fluorescence, and optically enhanced signals such as laser speckle-based images and/or videos, for the purpose of executing, analyzing, identifying, anticipating, and planning intended steps and avoiding unintended steps. The present disclosure further provides for real-time intraoperative machine learning-based guidance systems that may provide real time visual support before and/or during surgical procedures (e.g., dissection) on or near critical structures, so that surgical operators can identify relevant critical structures, assess tissue viability, and/or make surgical decisions during the operation. In some embodiments, such real-time machine learning-based guidance systems may also be implemented as a tool for ex post facto medical or surgical training. The present disclosure also provides for system with the capacity to autonomously or semi-autonomously track and update mobile and deformable tissue targets as tissue maneuvers are performed during a surgical operation or intervention.

In one aspect, the present disclosure provides a surgical guidance system comprising an image processing module configured to (i) receive image or video data obtained using one or more image and/or video acquisition modules and (ii) generate one or more medical predictions or assessments based on (a) the image or video data or physiological data associated with the image or video data and (b) one or more training data sets comprising surgical or medical data associated with a patient or a surgical procedure. The one or more training data sets may comprise anatomical and physiological data obtained using a plurality of imaging modalities. The system may further comprise a visualization module configured to provide a surgical operator with an enhanced view of a surgical scene, based on the one or more augmented data sets. In some embodiments, the enhanced view provided by the visualization module comprises information or data corresponding to the tissue viability for one or more tissue regions. In some embodiments, the information or data comprises quantitative measurements of tissue viability. In some embodiments, the visualization module is integrated with or operatively coupled to the image processing module.

In some embodiments, the one or more image and/or video acquisition modules comprise (i) a first image and/or video acquisition module configured to capture images and/or videos using a first imaging modality and (ii) a second image and/or video acquisition module configured to capture images and/or videos using a second imaging modality.

In some embodiments, the one or more medical predictions or assessments comprise an identification or a classification of one or more critical structures. In some embodiments, the one or more medical predictions or assessments comprise a predicted location of one or more critical structures. In some embodiments, the one or more medical predictions or assessments provide the surgical operator with predictive clinical decision support before and during a surgical procedure. In some embodiments, the one or more medical predictions or assessments are generated or updated in part based on an output of one or more computer vision algorithms. In some embodiments, the one or more medical predictions or assessments comprise medical information or live guidance that is provided to a user or an operator through one or more notifications or message banners. In some embodiments, the one or more medical predictions or assessments comprise tissue viability for one or more tissue regions in the surgical scene.

In some embodiments, the image processing module is configured to update or refine the one or more medical predictions or assessments in real time based on additional image data obtained during a surgical procedure. In some embodiments, the image processing module is configured to update or refine a predicted location of one or more critical structures in real time based on additional image data obtained during a surgical procedure.

In some embodiments, the one or more training data sets comprise medical data associated with one or more reference surgical procedures. In some embodiments, the one or more training data sets comprise medical data associated with (i) one or more critical phases or scenes of a surgical procedure or (ii) one or more views of a critical structure that is visible or detectable during the surgical procedure. In some embodiments, the one or more training data sets comprise medical data obtained using a laparoscope, a robot assisted imaging unit, or an imaging sensor configured to generate anatomical images and/or videos in a red-green-blue visual spectrum. In some embodiments, the one or more training data sets comprise medical data obtained using an imaging sensor configured to generate physiologic or functional imaging data based on chemical signal enhancers. In some embodiments, the chemical signal enhancers comprise ICG, fluorescent, or radiolabeled dyes. In some embodiments, the one or more training data sets comprise medical data obtained using an imaging sensor configured to generate physiologic or functional imaging data based on laser speckle patterns. In some embodiments, the one or more training data sets comprise medical data obtained using an imaging sensor configured to generate physiologic or functional imaging data. The physiologic or functional imaging data may comprise two or more co-registered images or videos. In some embodiments, the one or more training data sets comprise medical data obtained using an imaging sensor configured to generate physiologic or functional imaging data. The physiologic or functional imaging data may comprise segmented anatomic positions of critical structures of surgical interest. In some embodiments, the one or more training data sets comprise medical data obtained using a plurality of imaging modalities that enable direct objective correlation between physiologic images or videos and corresponding RGB images or videos. The plurality of imaging modalities may comprise depth imaging, distance mapping, intraoperative cholangiograms, angiograms, ductograms, ureterograms, or lymphangiograms. In some embodiments, the training data set comprises perfusion data.

In some embodiments, the image processing module is configured to update or refine the one or more medical predictions or assessments in real time based on additional physiologic data obtained during a surgical procedure. In some embodiments, the visualization module is configured to display and track a position and an orientation of one or more medical tools or critical features in real time. In some embodiments, the visualization module is configured to display a visual outline of the one or more critical features corresponding to predicted contours or boundaries of the critical features. In some embodiments, the image data obtained using one or more image and/or video acquisition modules comprises perfusion data. In some embodiments, the visualization module is configured to display a visual outline indicating a predicted location of one or more critical features before, during, or after the surgical operator performs one or more steps of a surgical procedure. In some embodiments, the visualization module is configured to autonomously or semi-autonomously track mobile and deformable tissue targets as tissue maneuvers are performed during a surgical procedure.

In some embodiments, the image processing module comprises a data multiplexer configured to combine anatomical and/or physiological data obtained using the one or more image and/or video acquisition modules. In some embodiments, the image processing module further comprises one or more feature extractors on spatial or temporal domains. The one or more feature extractors may be trained using the one or more training data sets and configured to extract one or more features from the combined anatomical and/or physiological data. In some embodiments, the one or more feature extractors comprise a spatial feature extractor configured to detect spatial features and generate a feature set for every image frame. In some embodiments, the spatial features comprise textures, colors, or edges of one or more critical structures. In some embodiments, the one or more feature extractors comprise a temporal feature extractor configured to detect a plurality of temporal features or feature sets over a plurality of image frames. In some embodiments, the temporal features correspond to changes in contrast, perfusion, or perspective.

In some embodiments, the image processing module further comprises a view classifier configured to use the one or more extracted features to determine a current surgical view relative to the surgical scene. In some embodiments, the image processing module further comprises a tissue classifier configured to use the one or more extracted features to identify, detect, or classify one or more tissues. In some embodiments, the image processing module further comprises a phase detector configured to use the one or more extracted features to determine a surgical phase and generate guidance based on the surgical phase. In some embodiments, the image processing module further comprises a critical structure detector configured to locate and identify one or more critical features based on (i) the one or more tissues identified, detected, or classified using the tissue classifier, (ii) a current surgical view determined using the view classifier, and (iii) the surgical phase determined using the phase detector. In some embodiments, the image processing module further comprises an augmented view generator configured to display guidance and metrics associated with the surgical procedure, based on the one or more critical features located and identified using the critical structure detector.

Another aspect of the present disclosure provides a non-transitory computer readable medium comprising machine executable code that, upon execution by one or more computer processors, graphical processing units and/or digital signal processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "real time" or "real-time," as used interchangeably herein, generally refers to an event (e.g., an operation, a process, a method, a technique, a computation, a calculation, an analysis, a visualization, an optimization, etc.) that is performed using recently collected or received data. In some cases, a real time event may be performed almost immediately or within a short time span, such as within at least 0.0001 millisecond (ms), 0.0005 ms, 0.001 ms, 0.005 ms, 0.01 ms, 0.05 ms, 0.1 ms, 0.5 ms, 1 ms, 5 ms, 0.01 seconds, 0.05 seconds, 0.1 seconds, 0.5 seconds, 1 second, or more. In some cases, a real time event may be performed almost immediately or within a short enough time span, such as within at most 1 second, 0.5 seconds, 0.1 seconds, 0.05 seconds, 0.01 seconds, 5 ms, 1 ms, 0.5 ms, 0.1 ms, 0.05 ms, 0.01 ms, 0.005 ms, 0.001 ms, 0.0005 ms, 0.0001 ms, or less.

The present disclosure provides systems and methods for providing real-time augmented surgical guidance to surgeons or medical personnel. The systems and methods disclosed herein may be implemented to provide predictive visualizations of critical structure locations and/or tissue viability based on machine learning (ML) recognition of surgical phase and content. In some cases, such predictive visualizations may be updated and/or refined based on newly acquired information (e.g., visual, anatomic, and/or physiological data). The systems and methods disclosed herein may also be implemented to provide real-time predictive decision support for analyzing, anticipating, planning, and executing steps in a surgical procedure while avoiding unintended, unrecognized, or unnecessary steps. In some cases, such predictive decision support may be based on ML recognition of surgical phase and content, and such ML recognition may be based on training using (i) data sets obtained using a plurality of imaging modalities and (ii) physiological data of a patient. The systems and methods of the present disclosure may be used for autonomous or semi-autonomous tracking of mobile and deformable tissue targets as tissue maneuvers are performed during a surgical procedure. In some cases, the system and methods of the present disclosure may be used to generate one or more procedure-specific ML-based models that are configured to identify or anticipate critical features, surgical phases, and/or procedure-specific guidance based on (i) imaging data obtained using a plurality of different imaging modalities and (ii) anatomical and/or physiological data of a patient. In some cases, such procedure-specific ML models may be further configured to generate an augmented view of a surgical scene that displays guidance/metrics to a surgeon or operating assistant.

Machine-Learning Based Predictions

The present disclosure generally relates to systems and methods for providing augmented visuals, real-time guidance, and decision support to surgeons and other operating assistants using artificial intelligence (AI). More specifically, the present disclosure relates to systems and methods for intraoperative real-time predictions of the locations of critical structures and/or tissue viability, and real-time anticipation and identification of critical structures and/or tissue viability in surgical procedures using machine learning algorithms. As used herein, tissue viability may refer to the ability of a tissue (or the cells of the tissue) to receive blood, nutrients, or other diffusible materials or substances which allow the tissue to stay alive and function in a normal manner. The machine learning algorithms may be trained on any combination of white light-based images and/or videos, chemical signal enhancers such as fluorescent near-infrared (NIR) images and/or videos or radio-labelled dye imaging, indigenous chromophores, autofluorescence, and optically enhanced signal such as laser speckle-based images and/or videos. The systems and methods of the present disclosure may be implemented for the purpose of identifying, planning, analyzing, and executing intended steps of a surgical procedure while avoiding unintended or unnecessary steps. The systems and methods of the present disclosure may be implemented to facilitate autonomous and/or semi-autonomous detection and tracking of mobile and deformable tissue targets over time as tissue maneuvers are performed during a surgical procedure.

Machine Learning

Machine learning may be used to implement the systems and methods of the present disclosure. As used herein, machine learning may refer to various functions, logic, and/or algorithms to teach a model to adapt, modify, and refine its decision making capabilities as the model is exposed to new data. In some cases, a model or rule set may be built and used to predict a result based on values of one or more features. One or more computing devices may be used to implement machine learning techniques and methods to build and/or train one or more models, functions or algorithms from an example training data set of input observations in order to make data-driven predictions or decisions expressed as outputs based on known properties learned from a training data set (rather than strictly following static programming instructions).

Machine learning may comprise a learning phase (i.e., a training phase) and an inference phase. During a training phase, one or more training data sets may be presented to the computing device for classification. In some cases, the one or more training data sets may comprise medical images and/or videos taken using a plurality of different imaging modalities. The actual result produced by the computing device may be compared against a known correct result, in some cases with reference to a function. A known correct result may be, e.g., a result that is predetermined to be correct by an expert in the field or based on evidence or collective agreement or concordance between anatomic and physiologic data. One objective of the training phase is to minimize discrepancies between known correct results and outputs by the computing device based on the one or more training data sets. Results from an output of the computing device may then be used to adjust certain parameters of the function and the computing device, in such a way that if another training data set were presented to the computing device another time, the computing device would theoretically produce a different output consistent with known correct results. Training of a computing device using machine learning methods may be complete when subsequent test data is presented to the computing device, the computing device generates an output on that test data, and a comparison between the output and known correct results yields a difference or value that is within a predetermined acceptable margin.

During the inference phase, one or more models trained during the training phase may be used to classify previously unclassified data. Such classifications may be performed automatically based on data input during a supervised portion of the machine learning process (i.e., the training phase). In the inference phase, medical data (e.g., live surgical anatomic and physiologic images and/or videos) may be parsed in accordance with a model developed during the training phase. Once the medical data has been parsed, the model may be used to classify one or more features contained or represented within the medical data. In some embodiments, this classification may be verified using supervised classification techniques (i.e., an editor may validate the classification). This classification may also be used as additional training data that is input into the training phase and used to train a new model and/or refine a previous model.

During the inference phase, medical data such as medical images and/or videos may be provided to the computing device. The computing device may be programmed to identify possible regions of interest, having been trained with a plurality of different training data sets comprising various medical images and/or videos. In some cases, the computing device may scan the medical images and/or videos, retrieve features from the medical images and/or videos, extract values from the medical images and/or videos, and match the values to predetermined values that the computing device has been programmed to recognize as being associated with various critical anatomic and physiologic features.

Machine Learning Algorithms

One or more machine learning algorithms may be used to implement the systems and methods of the present disclosures. The machine learning algorithm may be, for example, an unsupervised learning algorithm, supervised learning algorithm, or a combination thereof. The unsupervised learning algorithm may be, for example, clustering, hierarchical clustering, k-means, mixture models, DBSCAN, OPTICS algorithm, anomaly detection, local outlier factor, neural networks, autoencoders, deep belief nets, Hebbian learning, generative adversarial networks, self-organizing map, expectation-maximization algorithm (EM), method of moments, blind signal separation techniques, principal component analysis, independent component analysis, non-negative matrix factorization, singular value decomposition, or a combination thereof. In some embodiments, the supervised learning algorithm may be, for example, support vector machines, linear regression, logistic regression, linear discriminant analysis, decision trees, k-nearest neighbor algorithm, neural networks, similarity learning, or a combination thereof.

In some embodiments, the machine learning algorithm may comprise a deep neural network (DNN). In other embodiments, the deep neural network may comprise a convolutional neural network (CNN). The CNN may be, for example, U-Net, ImageNet, LeNet-5, AlexNet, ZFNet, GoogleNet, VGGNet, ResNet18, or ResNet, etc. In some cases, the neural network may be, for example, a deep feed forward neural network, a recurrent neural network (RNN), LSTM (Long Short Term Memory), GRU (Gated Recurrent Unit), Auto Encoder, variational autoencoder, adversarial autoencoder, denoising auto encoder, sparse auto encoder, boltzmann machine, RBM (Restricted BM), deep belief network, generative adversarial network (GAN), deep residual network, capsule network, or attention/transformer networks, etc. In some embodiments, the neural network may comprise neural network layers. The neural network may have at least about 2 to 1000 or more neural network layers. In some cases, the machine learning algorithm may be, for example, a random forest, a boosted decision tree, a classification tree, a regression tree, a bagging tree, a neural network, or a rotation forest.

The machine learning algorithms may be used to generate one or more medical models for predictive visualizations and/or predictive support during a surgical procedure. In some cases, the one or more medical models may be trained using neural networks or convolutional neural networks. In some cases, the one or more medical models may be trained using deep learning. In some cases, the deep learning may be supervised, unsupervised, and/or semi-supervised. In some cases, the one or more medical models may be trained using reinforcement learning and/or transfer learning. In some cases, the one or more medical models may be trained using image thresholding and/or color-based image segmentation. In some cases, the one or more medical models may be trained using clustering. In some cases, the one or more medical models may be trained using regression analysis. In some cases, the one or more medical models may be trained using support vector machines. In some cases, the one or more medical models may be trained using one or more decision trees or random forests associated with the one or more decision trees. In some cases, the one or more medical models may be trained using dimensionality reduction. In some cases, the one or more medical models may be trained using one or more recurrent neural networks. In some cases, the one or more recurrent neural networks may comprise a long short-term memory neural network. In some cases, the one or more medical models may be trained using one or more classical algorithms. The one or more classical algorithms may be configured to implement exponential smoothing, single exponential smoothing, double exponential smoothing, triple exponential smoothing, Holt-Winters exponential smoothing, autoregressions, moving averages, autoregressive moving averages, autoregressive integrated moving averages, seasonal autoregressive integrated moving averages, vector autoregressions, or vector autoregression moving averages.

Applications

The machine learning algorithms may be used to implement a real-time intraoperative AI guidance system that provides surgeons and medical personnel with visual support before, during, and/or after a surgical procedure. In one example, the real-time intraoperative guidance system may be used during a dissection or resection of tissues to aid a surgeon with anticipating and identifying relevant critical structures, evaluating or visualizing tissue viability, and/or providing options of surgical decisions during the surgical procedure. In another example, the real-time AI-based guidance system may provide anticipated identification of critical anatomy as an intraoperative decision support to the surgeon and/or the operating assistant(s) before and/or during a Calot triangle dissection during the removal of a medical subject's gall bladder (cholecystectomy). In another example, the real-time AI-based guidance system may be configured and/or used to provide information about tissue viability during surgical procedures.

The AI guidance system may be configured to obtain and evaluate new information about a patient's anatomy and/or physiology in real-time as dissection or resection progresses. The AI guidance system may be configured to make intraoperative predictions or assessments of (i) the location of relevant critical structures and/or (ii) tissue viability during one or more surgical procedures. The predictions of critical structure locations and/or tissue viability may begin prior to a dissection or resection of critical areas, and may be refined based on new information acquired by the system as further dissection or resection occurs.

In some cases, the AI guidance system may use perfusion data obtained using laser speckle contrast imaging to provide a surgeon with medical decision support during an operation. The system may also be used to predict the locations of critical structures and/or determine tissue viability for a given operative procedure. For example, in laparoscopic cholecystectomy, the system may be used to predict the location of one or more of the extrahepatic biliary structures, such as the cystic duct, cystic artery, common bile duct, common hepatic duct, and/or gallbladder. In other surgical procedures (e.g., surgical procedures on an organ, colorectal procedures, bariatric procedures, vascular procedures, endocrine procedures, otolaryngological procedures, urological procedures, gynecological procedures, neurosurgical procedures, orthopedics procedures, lymph node dissection procedures, procedures to identify a subject's sentinel lymph nodes, etc.), the system may be configured to provide surgical guidance and medical data analytics support by predicting and outlining the locations of critical structures and/or organs before, during, and/or after the surgical procedures, as well as tissue viability.

In one aspect, the present disclosure provides a real-time guidance and data analytics support system based on AI models that have been trained using one or more medical datasets corresponding to entire surgical procedures (or portions thereof). In some cases, the one or more medical data sets may comprise medical data pertaining to one or more critical phases or scenes of a surgical procedure, such as pre-dissection and post-dissection views of critical or vital structures. Such medical data may be obtained using (i) a scope, such as a laparoscope, (ii) a robot assisted imaging device, or (iii) any digital anatomic visual sensors in the red-green-blue visual, near-infrared, and/or short-wave infrared spectrums, and may include, in some non-limiting examples, physiologic or functional imaging data. In some cases, the imaging data may be based on chemical signal enhancers like indocyanine green (ICG), fluorescent or radiolabeled dyes, and/or optical signal enhancers based on coherent light transmissions, such as laser speckle imaging. In some cases, the imaging data may comprise two or more medical images and/or videos that are co-registered. In some cases, the imaging data may comprise one or more segmented medical images and/or videos indicating (1) anatomic positions of critical structures of surgical interest and/or (2) tissue viability. In any of the embodiments described herein, the medical data and/or the imaging data used to train the AI or machine learning models may be obtained using one or more imaging modalities, such as, for example, depth imaging or distance mapping. In some cases, information derived from depth imaging or distance mapping may be used to train the AI or machine learning models. The information derived from depth imaging may include, for example, distance maps that may be (1) calculated from disparity maps (e.g., maps showing the apparent pixel difference or motion between a pair of images or videos), (2) estimated using AI based monocular algorithms, or (3) measured using technologies such as time of flight imaging. In some cases, the one or more imaging modalities may alternatively or further include, for example, fluorescence imaging, speckle imaging, infrared imaging, UV imaging, X-ray imaging, intraoperative cholangiograms, angiograms, ductograms, ureterograms, and/or lymphangiograms. The use of such imaging modalities may allow for direct objective correlations between physiologic features and corresponding RGB images and/or videos.

The medical models described herein may be trained using physiologic data (e.g., perfusion data). The medical models may be further configured to process physiologic data and to provide real time updates. The addition of physiologic data in both training datasets and real time updates may improve an accuracy of medical data analysis, predictions for critical structure locations, evaluations of tissue viability, planning for surgical scene and content recognition, and/or execution of steps and procedural planning.

In some cases, the system may be configured to identify critical structures and visually outline the predicted contours and/or boundaries of the critical structures with a statistical confidence. In some cases, the system may be further configured to display, track, and update critical structure locations in real time a priori, at the onset of and/or during any surgical procedure based on a machine learning model-based recognition of surgical phase and content (e.g., tissue position, tissue type, or a selection, location, and/or movement of medical tools or instruments). The display and tracking of critical structure locations may be updated in real time based on medical data obtained during a surgical procedure, based on cloud connectivity and edge computing. As described elsewhere herein, the system may also be used to evaluate, assess, visualize, quantify, or predict tissue viability. In some cases, the system may be further configured to display notifications and/or informational banners providing medical inferences, information, and/or guidance to a surgeon, doctor, or any other individual participating in or supporting the surgical procedure (either locally or remotely). The notifications or message banners may provide information relating to a current procedure or step of the procedure to a surgeon or doctor as the surgeon or doctor is performing the step or procedure. The notifications or message banners may provide real time guidance or alerts to further inform or guide the surgeon or the doctor. The information provided through the notifications or message banners may be derived from the machine learning models described herein.

In some cases, the system may be configured to track a movement or a deformation of mobile and deformable tissue targets as tissue maneuvers are being performed during a surgical procedure. Such tracking may occur in an autonomous or semi-autonomous manner.

System Components

The system may be configured to use one or more procedure-specific machine learning models to provide surgical guidance. Each model may use a multi-stage approach, starting with a data multiplexer to combine anatomical and/or physiological data obtained from one or more medical imaging systems. The data multiplexer may be configured to combine all available data streams (e.g., data streams comprising medical information derived from medical imagery), with each stream allocated to its own channel. The system may further comprise one or more machine-learning based feature extractors. The one or more machine-learning based feature extractors may comprise a spatial feature extractor and/or a temporal feature extractor. The one or more machine-learning based feature extractors may be in a spatial and/or temporal domain and may be trained on pre-existing surgical data. The ML based spatial feature extractor may be used on each individual channel to find relevant features that may be combined to generate a feature set for every frame (which may correspond to one or more distinct time points). The ML based temporal feature extractor may be configured to take multiple such feature sets and extract the relevant features for the whole feature set. The ML based spatial feature extractor may be used to identify textures, colors, edges etc., while the ML based temporal feature extractor can indicate frame to frame changes, such as changes in contrast, perfusion, perspective, etc.

The extracted features described above may be used by ML classifiers trained on pre-existing data to (i) determine a surgical phase of an ongoing surgical procedure, (ii) predict or infer when a surgeon needs guidance, (iii) infer tissue types as a surgeon is viewing and/or operating on a target tissue or other nearby regions, and/or (iv) register the current surgical view to a known set of coordinates or reference frame. The classifications provided by the ML classifiers may be fed into a machine-learning based critical structure detector or tissue viability evaluator that can provide an augmented view generator with the required information to display guidance and metrics to a surgeon and/or one or more operating assistant(s) in real time during critical phases of a surgical procedure.

Figure 1:
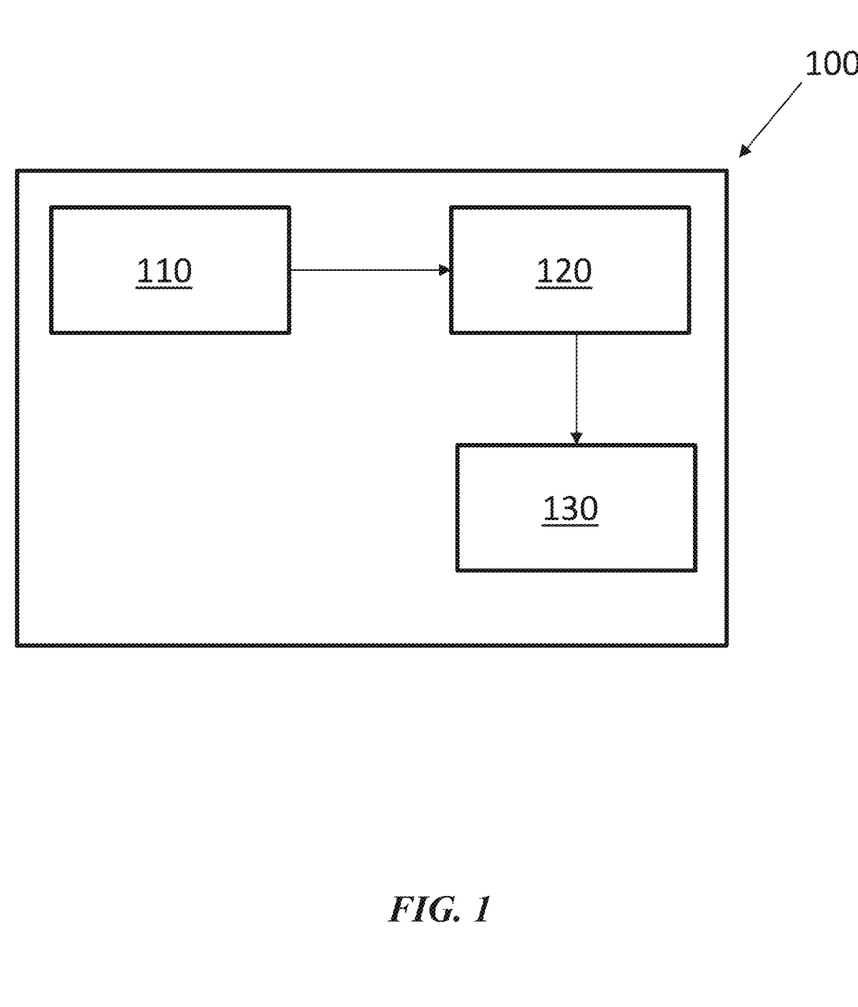
FIG. 1 schematically illustrates a system for providing medical or surgical guidance, in accordance with some embodiments.

FIG. 1 schematically illustrates a system 100 for providing medical or surgical guidance. The system 100 may comprise one or more imaging modules 110. The one or more imaging modules 110 may be used to obtain images and/or videos of a surgical procedure. The images and/or videos of the surgical procedure may comprise one or more tissue regions on or near which a surgeon or doctor is operating or preparing to operate. The one or more imaging modules 110 may be configured to provide the images and/or videos to an image and/or video processing module 120. The image and/or video processing module 120 may be configured to process the images and/or videos using any of the machine learning techniques described herein. The image and/or video processing module 120 may be configured to extract one or more spatial or temporal features from the images and/or videos. The one or more spatial or temporal features may be used to determine a surgical view, a tissue type, and/or a phase of a surgical procedure. The one or more spatial or temporal features (or one or more medical inferences derived from the features, such as tissue location, tissue movement, tissue viability, perfusion characteristics, etc.) may be provided to an augmented view generator 130. The augmented view generator 130 may be configured to provide real time guidance, metrics, and/or augmented image or video data to a surgeon during a surgical procedure.

Figure 2:
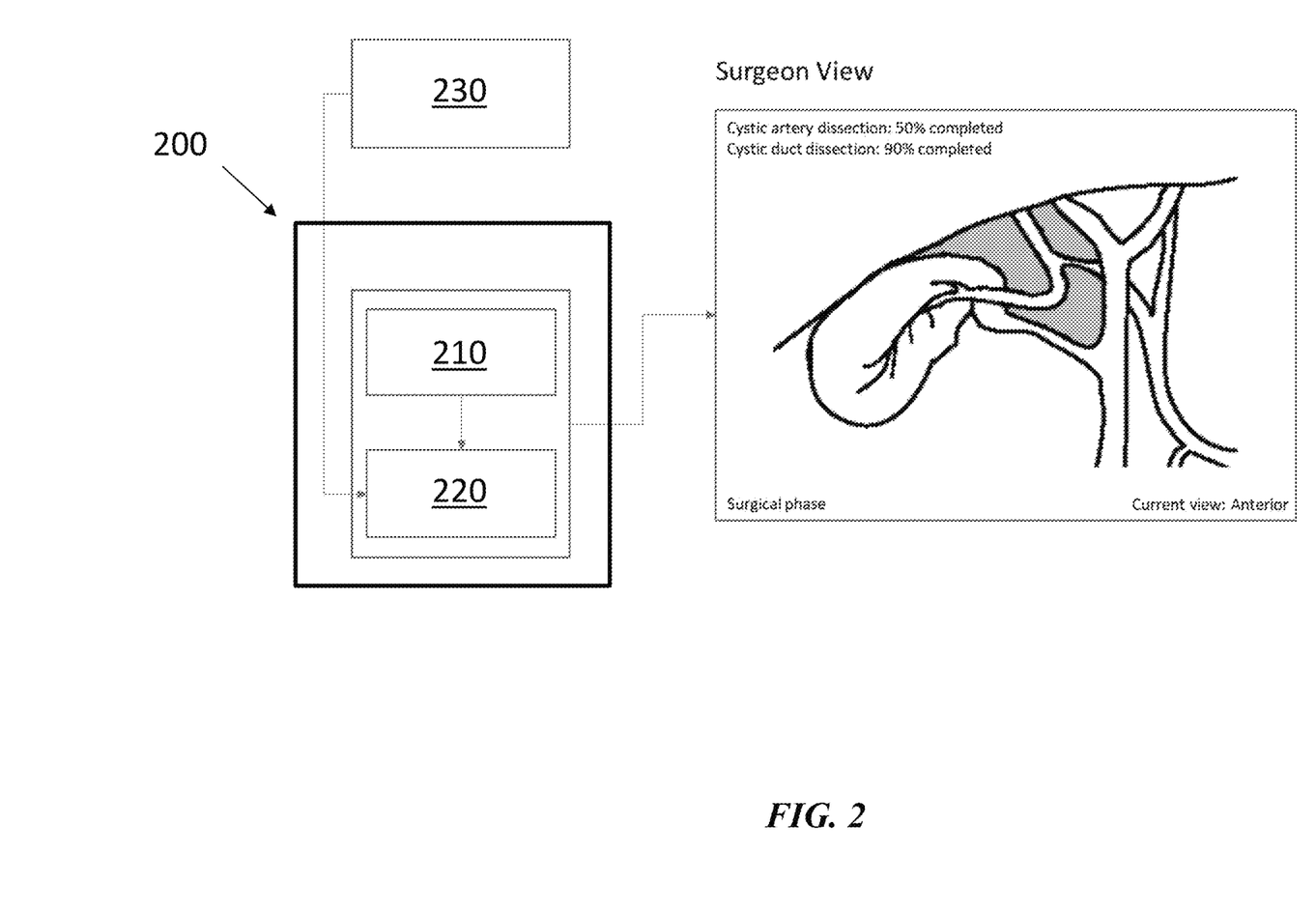
FIG. 2 schematically illustrates an overall system diagram for a medical guidance system, in accordance with some embodiments.

FIG. 2 provides an overall system diagram for a medical guidance system 200 as described herein. The medical guidance system 200 may comprise a near to far infrared image and/or video acquisition module 210 which may be configured to provide one input (e.g., a first input) to an image and/or video processing engine 220. In some cases, the image and/or video acquisition module 210 may be configured to acquire images and/or videos in the near infrared spectrum. In other cases, the image and/or video acquisition module 210 may be configured to acquire images and/or videos in the mid infrared spectrum. Alternatively, the image and/or video acquisition module 210 may be configured to acquire images and/or videos in the far infrared spectrum. In any of the embodiments described herein, the image and/or video acquisition module 210 may be configured to acquire images and/or videos in any portion or range of the infrared spectrum. As used herein, the infrared spectrum may correspond to a portion of the electromagnetic spectrum that is associated with light having a wavelength between about 700 nanometers (nm) and about 1 millimeter (mm). The second input may be provided by a laparoscopic imaging system 230 that may be separate from the medical guidance system 200 and the near infrared image and/or video acquisition module 210 of the medical guidance system 200. The image and/or video processing engine 220 may be configured to use artificial intelligence and/or machine-learning based inferences to provide augmented information to a surgeon. Such augmented information may comprise, for example, a current surgical step, an amount of progress for one or more steps of a surgical procedure, details about the current view (e.g., anterior view of a tissue, organ, or critical structure), and/or information about critical structures and tissue viability (e.g., perfusion characteristics).

Figure 3:
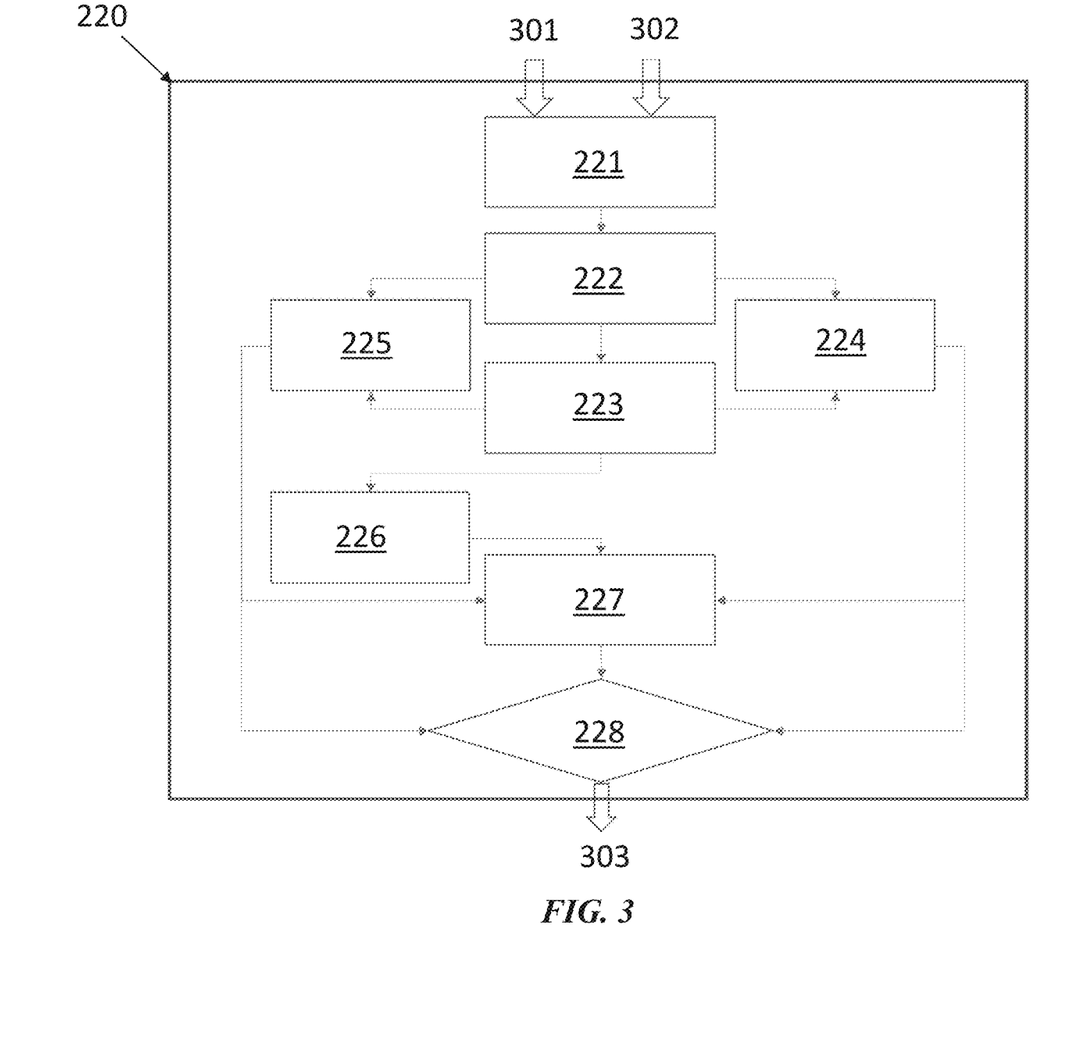
FIG. 3 schematically illustrates an internal diagram of an image processing engine, in accordance with some embodiments.

FIG. 3 schematically illustrates an internal diagram of the image and/or video processing engine 220 illustrated in FIG. 2. The image and/or video processing engine 220 may comprise a data multiplexer 221, a spatial feature extractor 222, a temporal feature extractor 223, a tissue classifier 224, a view classifier 225, a phase detector 226, a critical structure detector 227, and an augmented view generator 228.

The data multiplexer 221 may be configured to receive and combine at least a first data stream 301 and a second data stream 302. In some cases, the first data stream 301 may comprise laparoscopic imaging and/or video data, and the second data stream 302 may comprise infrared imaging and/or video data. The data multiplexer 221 may be configured to process the first data stream 301 and the second data stream 302 to generate combined data, which may be provided to the spatial feature extractor 222 and/or the temporal feature extractor 223. As described above, the spatial feature extractor 222 may be configured to find and/or extract relevant spatial features from the combined data and generate a feature set for every frame corresponding to one or more distinct time points. The spatial features may comprise scene information (e.g., a presence or an absence of one or more features in a surgical scene), tool information (e.g., a position and/or an orientation of a tool relative to the surgical scene), and/or real-time updates of a position, orientation, shape, structure, or deformation of one or more tissue regions of interest. The temporal feature extractor 223 may be configured to take multiple feature sets identified by the spatial feature extractor 222 and extract relevant temporal features for the whole feature set to track changes to the features over a period of time. As described above, the spatial feature extractor 222 may be used to identify textures, colors, edges etc., while the temporal feature extractor 223 can be used to determine or visualize frame to frame changes to one or more spatial features, such as changes in contrast, perfusion, perspective, etc.

The extracted features described above may be provided to one or more machine-learning based classifiers trained on pre-existing data. For example, the extracted features may be provided to a tissue classifier 224 that is configured to use the extracted features to infer tissue types as a surgeon is viewing and/or operating on a target tissue or other nearby regions. The extracted features may also be provided to a view classifier 225 that is configured to use the extracted features to determine a current surgical view relative to a known set of coordinates or reference frame, or to register the current surgical view to a known set of coordinates or reference frame. The extracted features may also be provided to a phase detector 226 that is configured to use the extracted features to determine a surgical phase of an ongoing surgical procedure. The outputs or inferences generated by the tissue classifier 224, the view classifier 225, and the phase detector 226 may be provided to a critical structure detector 227 that is configured to use the outputs or inferences to detect one or more critical structures, determine a location of the one or more critical structures, and/or identify one or more biological or physiological characteristics associated with one or more critical structures (e.g., perfusion and/or tissue viability). The critical structure detector 227 may be operatively coupled to an augmented view generator 228 that is configured to predict or infer when a surgeon needs guidance, and display an augmented surgical view 303 comprising guidance and metrics to a surgeon and/or one or more operating assistant(s) in real time during critical phases of a surgical procedure.

Computer Vision

In some non-limiting embodiments, one or more computer vision algorithms may be used to implement the systems and methods of the present disclosure. The one or more computer vision algorithms may be used in combination with machine learning to enhance the quality of medical inferences generated. Alternatively, the one or more computer vision algorithms may be used in place of machine learning to provide different kinds or types of medical inferences.

In some cases, the one or more computer vision algorithms may comprise, for example, an object recognition or object classification algorithm, an object detection algorithm, a shape recognition algorithm and/or an object tracking algorithm. In some cases, the computer vision algorithm may comprise computer implemented automatic image recognition with pixel and pattern analysis. In other cases, the computer vision algorithm may comprise machine vision processes that involve different kinds of computer processing such as object and character recognition and/or text and visual content analysis. In some embodiments, the computer vision algorithm may utilize machine learning or may be trained using machine learning. Alternatively, the computer vision algorithm may not or need not utilize machine learning or machine-learning based training.

Computer Systems

Figure 4:
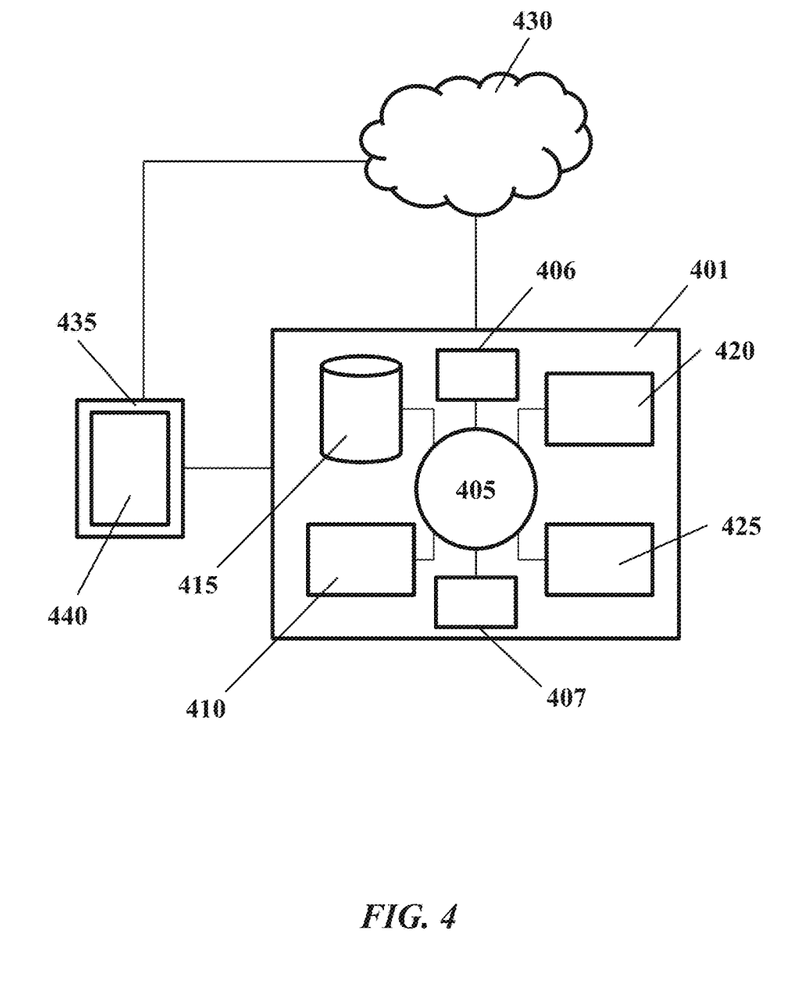
FIG. 4 schematically illustrates a computer system that is programmed or otherwise configured to implement methods provided herein.

In an aspect, the present disclosure provides computer systems that are programmed or otherwise configured to implement methods of the disclosure, e.g., any of the subject methods for providing surgical guidance. FIG. 4 shows a computer system 401 that is programmed or otherwise configured to implement a method for providing surgical guidance. The computer system 401 may be configured to, for example, combine data streams obtained from one or more medical imaging units, extract one or more spatial or temporal features from the combined data streams, classify the features, and generate an augmented surgical view using the classifications to provide surgeons and medical personnel with real time guidance and metrics during critical phases of a surgical procedure. The computer system 401 can be an electronic device of a user or a computer system that is remotely located with respect to the electronic device. The electronic device can be a mobile electronic device. In some instances, a single computer system or computing device may be used for delivering information to a surgeon, performing image and/or video acquisition, training or running one or more machine learning models, and/or generating medical inferences based on the one or more machine learning models. In other instances, a plurality of computer systems or computing devices may be used to perform different functions (including, for example, delivering information to a surgeon, performing image and/or video acquisition, training or running one or more machine learning models, and/or generating medical inferences based on the one or more machine learning models). Utilizing two or more computer systems or computing devices may enable parallel processing of tasks or information to provide real time surgical inferences and/or machine learning based surgical guidance.

The computer system 401 may include a central processing unit (CPU, also "processor" and "computer processor" herein) 405, which can be a single core or multi core processor, or a plurality of processors for parallel processing. The computer system 401 may also include one or more graphical processing units (GPUs) 406 and/or digital signal processors (DSPs) 407, memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are located external to the computer system 401 (e.g., on a remote server that is in communication with the computer system 401 through an intranet or the Internet).

The computer system 401 can communicate with one or more remote computer systems through the network 430. For instance, the computer system 401 can communicate with a remote computer system of a user (e.g., a doctor, a surgeon, a medical worker assisting or performing a surgical procedure, etc.). Examples of remote computer systems include personal computers (e.g., portable PC), slate or tablet PC's (e.g., Apple® iPad, Samsung® Gala4 Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, an augmented surgical view portal for a doctor or a surgeon to view surgical guidance or metrics in real time during a surgical procedure. The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 405. For example, the algorithm may be configured to combine data streams obtained from one or more medical imaging units, extract one or more spatial or temporal features from the combined data streams, classify the features, and generate an augmented surgical view using the classifications to provide surgeons and medical personnel with real time guidance and metrics during critical phases of a surgical procedure.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A surgical guidance system comprising:
   an image processing module configured to,
   (i) receive image or video data obtained using one or more image and/or video acquisition modules; and
   (ii) generate one or more medical predictions or assessments based on,
      (a) the image or video data or physiological data associated with the image or video data; and
      (b) one or more training data sets including medical data associated with one or more reference surgical procedures, wherein the one or more training data sets include anatomical and physiological data obtained using a plurality of imaging modalities, wherein the one or more training data sets include medical data obtained using the plurality of imaging modalities that enable direct objective correlation between physiologic images or videos and corresponding red-green-blue (RGB) images or videos, wherein the plurality of imaging modalities include depth imaging, distance mapping, intraoperative cholangiograms, angiograms, ductograms, ureterograms, or lymphangiograms; and
   a visualization module configured to provide a surgical operator with an enhanced view of a surgical scene, based on the one or more training data sets.

2. The system of claim 1, wherein the one or more image and/or video acquisition modules comprise (i) a first image and/or video acquisition module configured to capture images or videos using a first imaging modality and (ii) a second image or video acquisition module configured to capture images and/or videos using a second imaging modality.

3. The system of claim 1, wherein the one or more medical predictions or assessments comprise an identification or a classification of a critical structure or a predicted location of the critical structure or provide the surgical operator with predictive clinical decision support before and during a surgical procedure.

4. The system of claim 1, wherein the image processing module is configured to update or refine the one or more medical predictions or assessments in real time based on additional image data obtained during a surgical procedure.

5. The system of claim 4, wherein the image processing module is configured to update or refine a predicted location of a critical structure in real time based on additional image data obtained during the surgical procedure.

6. The system of claim 1, wherein the one or more training data sets comprise medical data obtained using a laparoscope, a robot assisted imaging unit, or an imaging sensor configured to generate anatomical images and/or videos in a RGB visual spectrum.

7. The system of claim 1, wherein the one or more training data sets comprise medical data obtained using an imaging sensor configured to generate physiologic or functional imaging data based on chemical signal enhancers, wherein the chemical signal enhancers include indocyanine green (ICG), fluorescent, or radiolabeled dyes.

8. The system of claim 1, wherein the one or more training data sets comprise medical data obtained using an imaging sensor configured to generate physiologic or functional imaging data based on laser speckle patterns.

9. The system of claim 1, wherein the one or more training data sets comprise medical data obtained using an imaging sensor configured to generate physiologic or functional imaging data, wherein the physiologic or functional imaging data includes two or more co-registered images or videos.

10. The system of claim 1, wherein the one or more training data sets comprise medical data obtained using an imaging sensor configured to generate physiologic or functional imaging data, wherein the physiologic or functional imaging data includes segmented anatomic positions of a critical structure.

11. The system of claim 1, the one or more training data sets comprise medical data associated with (i) one or more critical phases or scenes of a surgical procedure or (ii) one or more views of a critical structure that is visible or detectable during the surgical procedure.

12. The system of claim 1, wherein the image processing module is configured to update or refine the one or more medical predictions or assessments in real time based on additional physiologic data obtained during a surgical procedure.

13. The system of claim 1, wherein the visualization module is configured to display and track a position and an orientation of one or more medical tools or one or more critical features in real time or wherein the visualization module is configured to display a visual outline of the one or more critical features corresponding to predicted contours or boundaries of the one or more critical features.

14. The system of claim 1, wherein the one or more training data sets comprises perfusion data.

15. The system of claim 1, wherein the image data obtained using one or more image and/or video acquisition modules comprises perfusion data.

16. The system of claim 1, wherein the visualization module is configured to display a visual outline indicating a predicted location of one or more critical features before, during, or after the surgical operator performs one or more steps of a surgical procedure, or autonomously or semi-autonomously track mobile and deformable tissue targets as tissue maneuvers are performed during the surgical procedure.

17. The system of claim 1, wherein the image processing module comprises a data multiplexer configured to combine the anatomical or physiological data obtained using the one or more image or video acquisition modules.

18. The system of claim 1, wherein the image processing module further comprises one or more feature extractors on spatial or temporal domains, wherein the one or more feature extractors are trained using the one or more training data sets and configured to extract one or more features from the anatomical and physiological data.

19. The system of claim 18, wherein the one or more feature extractors comprise:
  a spatial feature extractor configured to detect spatial features and generate a feature set for every image frame;
  a temporal feature extractor configured to detect a plurality of temporal features or feature sets over a plurality of image frames;
  a view classifier configured to use the one or more extracted features to determine a current surgical view relative to the surgical scene;
  a tissue classifier configured to use the one or more extracted features to identify, detect, or classify one or more tissues; or
  a phase detector configured to use the one or more extracted features to determine a surgical phase and generate guidance based on the surgical phase.

20. The system of claim 1, wherein the visualization module is integrated with or operatively coupled to the image processing module.

21. The system of claim 1, wherein the one or more medical predictions or assessments comprises:
  medical information or live guidance that is provided to a user or the surgical operator through one or more notifications or message banners;
  tissue viability for one or more tissue regions in the surgical scene; or
  information generated or updated in part based on an output of one or more computer vision algorithms.

* * * * *

UNITED STATES PATENT AND TRADEMARK OFFICE
CERTIFICATE OF CORRECTION

PATENT NO. : 12,131,818 B2
APPLICATION NO. : 18/323623
DATED : October 29, 2024
INVENTOR(S) : Bogdan Mitrea et al.

Page 1 of 1

It is certified that error appears in the above-identified patent and that said Letters Patent is hereby corrected as shown below:

In the Claims

Column 17, Claim 1, Line 28:
more image and/or video acquisition modules; and
Should read:
more image or video acquisition modules; and Column 17, Claim 2, Lines 52-53:
and/or video acquisition modules comprise (i) a first image
and/or video acquisition module configured to capture
Should read:
or video acquisition modules comprise (i) a first image
or video acquisition module configured to capture Column 17, Claim 2, Line 56:
capture images and/or videos using a second imaging
Should read:
capture images or videos using a second imaging Column 18, Claim 6, Line 8:
configured to generate anatomical images and/or videos in a
Should read:
configured to generate anatomical images or videos in a Column 18, Claim 15, Line 51:
obtained using one or more image and/or video acquisition
Should read:
obtained using one or more image or video acquisition Signed and Sealed this
Sixteenth Day of December, 2025

John A. Squires
*Director of the United States Patent and Trademark Office*